United States Patent [19]

Sanoian

[11] Patent Number: 4,495,518
[45] Date of Patent: Jan. 22, 1985

[54] INFRARED TEST FOR WOODEN UTILITY POLES FOR STRUCTURAL SOUNDNESS

[76] Inventor: Corigan Sanoian, 682 Orchard Pkwy., Niagara Falls, N.Y. 14301

[21] Appl. No.: 433,002

[22] Filed: Oct. 6, 1982

[51] Int. Cl.$^3$ .............................................. H04N 5/23
[52] U.S. Cl. ..................................... 358/113; 358/106; 250/333
[58] Field of Search ................ 358/106, 113; 250/330, 250/332, 334, 331, 333, 341, 340, 358.1, 359.1, 339, 342, 338

[56] References Cited

U.S. PATENT DOCUMENTS

| | | | |
|---|---|---|---|
| 2,606,294 | 8/1952 | Hagan | 250/338 |
| 4,328,516 | 5/1982 | Colpack et al. | 358/113 |
| 4,338,627 | 7/1982 | Stapleton | 358/113 |
| 4,347,530 | 8/1982 | Stetson | 358/113 |

Primary Examiner—John C. Martin
Assistant Examiner—John K. Peng
Attorney, Agent, or Firm—Raymond F. Kramer

[57] ABSTRACT

A method for testing wooden utility poles for structural soundness, which quickly indicates usual structural conditions which make the pole unsound, such as rot, porosity and internal cavities, includes converting infrared radiation received from a utility pole being tested to visually observable form, comparing such radiation in such form, as received from different locations along the length of the utility pole, and noting disparities therein, which indicate portions of a pole which may be structurally unsound. The infrared radiation is converted to visually observable form by means of a cathode ray tube and appropriate optical and electronic transducers and circuitry, the infrared pattern is viewed by an operator of the equipment, sometimes preferably with a plurality of views of the pole being observed, and photographs of the cathode ray tube display are taken for future reference and study. In highly preferred embodiments of the invention the equipment is mounted on a motor vehicle, such as a panel truck or van, which traverses a roadway along which the utility poles are located, and for best results the testing is carried out at certain hours at which most significant differences can be observed between structurally sound and unsound portions of the poles.

10 Claims, 3 Drawing Figures

U.S. Patent   Jan. 22, 1985   4,495,518

INFRARED TEST FOR WOODEN UTILITY POLES FOR STRUCTURAL SOUNDNESS

BACKGROUND OF THE INVENTION

Field of the Invention

This invention relates to a method for testing wooden utility poles to determine whether they are structurally sound. More particularly, it relates to a method in which infrared radiation emanating from the length of a utility pole or a substantial proportion thereof is converted to visible form, such radiation is viewed, and disparities in the infrared radiation and/or visible patterns thereof are noted (which usually indicate structurally unsound areas of a pole, such as those wherein the wood has rotted or become porous, or in which internal cavities are present).

Description of the Prior Art

The problems that are caused by fallen utility poles are well known and therefore concerted efforts have been made to make sure that such poles are structurally sound and will not be toppled during storms or under "normal" stress conditions. In a modern society blockings of roadways and interruptions of utility services are serious enough events that it has been considered that utilities are strictly accountable for satisfactorily inspecting utility poles and maintaining them in sound condition. Preventive maintenance, which includes pressure treating of the poles before installation, and often includes subsequent treatments thereof, has been very useful but despite such treatments wooden poles are subject to attack by insects, fungi, bacteria, disease, and boring and nesting birds, such as woodpeckers. Often any weakness caused in the pole will be invisible or almost invisible. Accordingly, visual inspection, although sometimes useful, will often not disclose whether a wooden utility pole is structurally unsound and potentially hazardous.

Physical testings of poles have been carried out, with borings being made and bore samples or cores being inspected, but this is a time-consuming procedure and it tends to weaken the pole. Also, unless the bored out material is replaced the bore holes may actually act as favored sites for the promotion of disease, insect attacks, etc. Some non-destructive methods of testing wooden utility poles for structural defects require the physical attachments of contacts, tranducers or other means at different locations along the length of the pole, and therefore are time consuming. The importance of quick evaluations of utility poles and the avoidance of climbing the pole to set equipment in place are evident when the magnitude of the inspection problem is appreciated. Thus, for example, a utility the size of Detroit Edison has about 1,000,000 wooden poles supporting about 35,000 miles of utility lines. If in an eight hour day a crew could inspect one pole every twenty minutes it would take 55 crews to inspect every pole once every three years. On the other hand, if the inspection time, including transportation between poles, would take only five minutes per pole (and by using the present method even less time has been averaged), the number of crews could be reduced to fourteen. Furthermore, the present method lends itself to operation by a single driver-operator if the video screen is located where he can readily view it and operate it from the vehicle cab or driver's seat.

The closest art known to the inventor relates to work such as that previously done by him in which he employed infrared technology to detect defective portions of builtup roofing structures. Also, he recognizes that infraredsensitive systems wherein infrared energy is converted to video or CRT displays are known, such as those described in U.S. Pat. Nos. 4,328,516; 4,338,627; and 4,347,530. Additionally, he is aware that infrared rays have been employed for the physical testings of various materials, such as welded steel. Yet, he considers that before his invention there was no disclosure of the employment of "infrared television" for the improved structural testing of wooden utility poles and he considers that such invention is unobvious from the prior art known to him.

SUMMARY OF THE INVENTION

In accordance with the present invention a method for testing a wooden utility pole for structural soundness comprises receiving infrared radiation from a wooden utility pole being tested, converting the infrared radiation received to visually observable form, comparing by means of such visually observable forms radiation received from different locations along the length of the utility pole, and noting disparities therein, which are indicative of portions of the pole which may be structurally unsound. Preferably, the visually observable form of infrared radiation is a picture of a utility pole on a cathode ray tube, with disparities therein indicating variations in structural soundness. The method is preferably employed at particular times when it has been found that the infrared signal contrasts are greatest, photographs of the video screen are preferably taken for records, different views of the same pole, from different angles are preferably taken and the equipment is mounted on a motor vehicle, from which it is operated to test the utility poles along the road on which a vehicle is driven.

BRIEF DESCRIPTION OF THE DRAWINGS

The invention will be readily understood by reference to the specification and the following description, taken in conjunction with the drawing, in which.

DETAILED DESCRIPTION OF THE DRAWINGS

Figure 1:
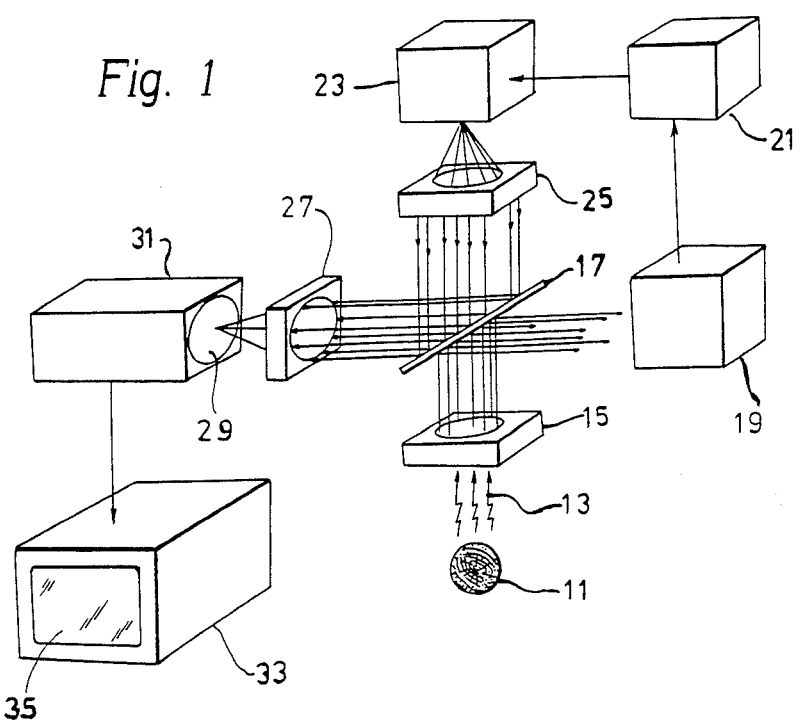
FIG. 1 is a simplified block form schematic representation of suitable apparatus for carrying out the method of this invention, illustrating how infrared rays emanating from a wooden utility pole being tested are converted to a visual image on a cathode ray tube.

In FIG. 1 wooden utility pole 11, seen from the top thereof, is shown emitting infrared radiation, represented by arrows 13, which are focused by infrared optics 15 onto one side of scanning mirror 17, which reflects the infrared energy onto an infrared detector array 19. From the cryogenically cooled array 19 electrical signals, produced by the array from the infrared energy, are amplified by amplifier 21 and are fed to a light-emitting diode array 23 which converts the signals to light in the visible range and produces a pattern corresponding to the portion of the utility pole viewed (preferably the height of the pole). The light from the LED array is received by an optical coupling system, including a visual collimator 25 which converts the diverging light rays projected from the LED array 23 into substantially parallel light rays, which are subsequently reflected by the opposite side of scanning mirror 17 through an optical lens system 27, which focuses the light onto the light-sensitive target 29 of a vidicon tube assembly 31. The vidicon 31 drives a cathode ray tube (CRT) display 33, which will show a view of the infrared emanations from the utility pole on screen 35 thereof.

Figure 2:
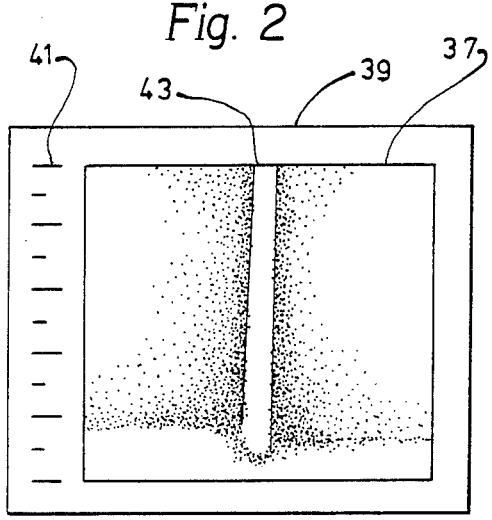
FIG. 2 is a view of a photograph of the cathode ray tube of FIG. 1 with a portion of a structurally sound wooden utility pole shown thereon.

In FIG. 2 photograph 37, mounted on backing sheet 39, which includes indicia 41 along a margin thereof for ease of location and identification of reference portions of the photograph, shows an illustration of a wooden utility pole 43 which appears to be in sound condition. In other words, the image of the pole, which indicates the infrared emanations from it, is regular, with no significant discontinuities or disparities being apparent.

Figure 3:
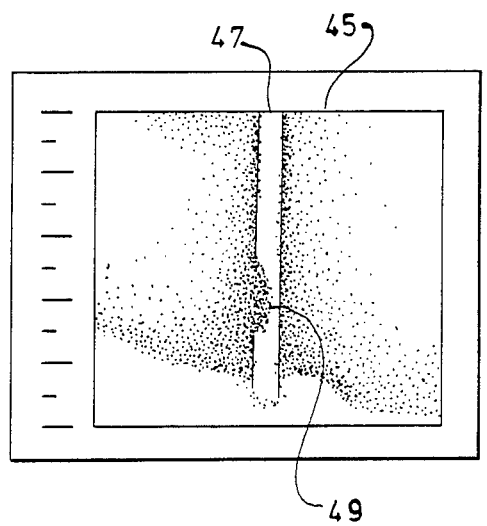
FIG. 3 is a view like that of FIG. 2 but showing a portion of a utility pole which includes a structurally unsound portion.

In FIG. 3 photograph 45 shows an image 47 of a wooden utility pole wherein there is an area 49 which is substantially different in appearance from the rest of the image of the pole, indicating a difference in the transmission from such area of infrared radiation and indicating that such area should be checked further for structural unsoundness (and that the pole is probably structurally unsound at such location).

The invention is readily employed and the process is easily practiced. All that is necessary is for a suitable "infrared television" camera, a cathode ray tube display or video screen, and the intermediate equipment described (which are commercially available) to be mounted on a suitable vehicle, preferably in a van or on a panel truck, so that the camera can scan utility poles along the path of the vehicle. Exemplary of the equipment mentioned is that described in the patents previously mentioned in this specification, which are hereby incorporated by reference.

It has been found that best results are obtainable when the scanning is done within a period from sunset to six hours thereafter, preferably from an hour after sunset to four hours thereafter, or less preferably but acceptably, during a period from an hour after sunrise to six hours thereafter, preferably from two to five hours after sunrise. At such times it appears that the infrared transmission from sound and unsound portions of wooden utility poles is most significantly different and accordingly the contrasts showing up on the video screen and in photographs of it which may be taken will be greater.

While it is preferred for the vehicle on which the equipment is mounted to be stopped at each pole being viewed, it is within the invention for such examinations to be made while the vehicle is in motion. Also, while it is preferred to take at least two "pictures" of a pole being tested, preferably at about 90° to each other (as the camera approaches and as it leaves the pole), it is within the invention to take only one such view, which usually will be from directly in front of the pole. Actual views of the pole being inspected are preferred but it is within the invention to enhance such views by electronic circuitry and other modifications, by the employment of special filters and by color (or black-and-white) reversal. Also, while black-and-white television is normally considered satisfactory it is within the invention to convert portions of the infrared spectrum to different colors and to take color pictures of the TV screen.

Alternatively, instead of projecting pictures of the pole, there may be produced on the video screen representations of infrared emissions from the pole, according to wave length, amplitude or combinations of both. In short, various devices and mechanisms may be employed to visibly accentuate differences in infrared emissions from the utility pole.

While this invention is not limited by the following theory as to the basis for its effectiveness (and applicant is not bound by such theory), it is considered useful to explain the unexpectedly beneficial results that have been obtained. It seems that wooden utility poles tend to absorb different proportions of moisture depending on their internal structures and such internal structure varies depending on the soundness of the pole. Accordingly, infrared patterns from the pole will vary depending on the soundness of the pole. The presence of rot, porous sections, and hollows, such as squirrels'0 or birds' nests, will emit characteristically different infrared patterns from sounder wooden sections and such differences can be detected by means of the infrared video camera and display. Also, the loss of heat or gain or heat varies, depending on the internal structure of the wooden pole and therefore at certain hours of the day or night, as mentioned above, greatest differences in infrared emitting properties are capable of being observed (because then the pole is either losing or gaining heat).

In actual use, the described apparatus and the present method have proven to be startlingly successful. Examinations of utility poles have been effected in five minutes or less using the described equipment (including AGA Thermovision ®), and in most cases it has been found that a single "view" of the pole, using a black-and-white CRT display, has been sufficient to determine whether the pole is a candidate for additional examination, as by taking bore samples, or is in sound condition. Poles bored are confirmed to be unsound, if clearly indicated as such by the described method. Because different camera and display equipment setups are of different sensitivities (and sometimes are idiosyncratic), the operator will normally be able to perfect his technique as he becomes more used to the equipment to which he is assigned. He will be able to improve in ability of sensitizing the equipment so as to enable him better to discriminate between sound and unsound poles, and specific portions thereof. He will also become more adept at utilizing and directing the infrared camera portion of the equipment and to operating the vehicle on which it is mounted, in conjunction with taking pictures of the utility poles.

In some instances receiving the infrared emanations from the pole will be improved by having the infrared sensitive camera mounted on means which will move vertically while scanning the pole but such, while desirable, has not been found to be necessary for the useful practicing of the invention. The described controlled height scanner may be operable by the vehicle operator or by a scanning technician, and the screen may be viewed by either or both. The described mechanical features, because they relate to auxiliary equipment for use with the present invention and because they are considered to be evident from this description, are not specifically illustrated in the drawing, which is directed to more significant aspects of the invention.

The invention has been described with respect to preferred embodiments and illustrations thereof but is not to be limited to these because it is evident that one of skill in the art, with the present specification before him, will be able to utilize substitutes and equivalents without departing from the invention. Thus, the invented process may under some circumstances be applicable to testing wooden pole-like structures, such as bridge posts, sign supports, ship masts and flag poles.

What is claimed is:

1. A method for testing a wooden utility pole for structural soundness which comprises receiving infrared radiation from a wooden utility pole being tested, converting the infrared radiation received to visually observable form, comparing by means of such visually observable form radiation received from different locations along the length of the utility pole, and noting disparities therein, which are indicative of portions of the pole which may be structurally unsound.

2. A method according to claim 1 wherein the infrared radiation is received during a time between sunset and six hours thereafter or between an hour after sunrise and six hours thereafter.

3. A method according to claim 2 wherein the infrared radiation is converted to visually observable form on the screen of a cathode ray tube.

4. A method according to claim 3 wherein a series of wooden utility poles is tested, disparities in the CRT displays relevant to the individual poles are noted, pictures are taken of the displays of poles showing such disparities, such pictures are identified by indicia to relate them to the particular poles tested and the pictures are referred to for locating portions of the poles to be subjected to physical testing to establish the nature and extent of any structurally unsound condition of the pole.

5. A method according to claim 4 wherein the testing is carried out during a time between an hour after sunset and four hours thereafter or two hours after sunrise and five hours thereafter.

6. A method according to claim 5 wherein borings are taken of the poles in the locations thereof exhibiting disparities in the CRT displays.

7. A method according to claim 6 wherein the receiving of the infrared radiation, conversion to visually observable form, comparison of the radiation received from different locations along the pole and noting of the disparities are effected on a vehicle which may readily be driven along a road adjacent to a series of utility poles so that testings thereof may be carried out expeditiously.

8. A method according to claim 7 wherein the receiving of infrared radiation from the utility pole being tested is at a plurality of times during the testing and is from a plurality of different surface portions thereof, each being along a substantial proportion of the pole, so that a plurality of infrared radiation patterns from the pole is obtainable to better indicate whether the pole is structurally unsound.

9. A method according to claim 1 wherein the receiving of the infrared radiation, conversion to visually observable form, comparison of radiation received from different locations along the pole and noting of the disparity are effected on a movable vehicle which may readily be driven along a road adjacent to a series of utility poles so that testings thereof may be carried out expeditiously.

10. A method according to claim 1 wherein the receiving of infrared radiation from the utility pole being tested is at a plurality of times during the testing and is from a plurality of different surface portions thereof, each being along a substantial proportion of the pole, so that a plurality of infrared radiation patterns from the pole is obtainable to better indicate whether the pole is structurally unsound.

* * * * *